US008491546B2

(12) United States Patent
Hoang et al.

(10) Patent No.: US 8,491,546 B2
(45) Date of Patent: Jul. 23, 2013

(54) PATIENT FLUID LINE ACCESS VALVE ANTIMICROBIAL CAP/CLEANER

(75) Inventors: Minh Quang Hoang, Sandy, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 248 days.

(21) Appl. No.: 12/802,512

(22) Filed: Jun. 8, 2010

(65) Prior Publication Data

US 2010/0242993 A1    Sep. 30, 2010

Related U.S. Application Data

(62) Division of application No. 11/281,711, filed on Nov. 17, 2005.

(51) Int. Cl.
*A61M 25/16* (2006.01)
*A61M 25/00* (2006.01)

(52) U.S. Cl.
USPC ............................... 604/267; 604/533

(58) Field of Classification Search
USPC ....................... 604/533, 265, 267
See application file for complete search history.

(56) References Cited

U.S. PATENT DOCUMENTS

| 2,961,682 | A |   | 11/1960 | Wurmbock |
| 4,282,891 | A |   | 8/1981  | Duceppe |
| 4,354,490 | A |   | 10/1982 | Rogers |
| 4,432,764 | A |   | 2/1984  | Lopez |
| 4,440,207 | A | * | 4/1984  | Genatempo et al. .......... 150/154 |
| 4,444,310 | A | * | 4/1984  | Odell .............................. 206/366 |
| 4,624,664 | A |   | 11/1986 | Peluso et al. |
| 4,626,664 | A | * | 12/1986 | Grise ............................. 219/525 |
| 4,655,762 | A |   | 4/1987  | Rogers |
| 4,671,306 | A |   | 6/1987  | Spector |
| 4,778,447 | A | * | 10/1988 | Velde et al. ..................... 604/29 |
| 5,195,957 | A |   | 3/1993  | Tollini |
| 5,242,425 | A | * | 9/1993  | White et al. ................... 604/256 |
| 5,334,388 | A |   | 8/1994  | Hoang et al. |
| 5,547,662 | A | * | 8/1996  | Khan et al. ................. 424/78.03 |
| 5,554,135 | A | * | 9/1996  | Menyhay ....................... 604/256 |
| 5,639,310 | A |   | 6/1997  | Giampaolo, Jr. |
| 5,641,464 | A |   | 6/1997  | Briggs, III et al. |
| 5,694,978 | A |   | 12/1997 | Heilmann et al. |
| 5,706,944 | A | * | 1/1998  | Hoang et al. ................... 206/438 |
| 5,722,537 | A |   | 3/1998  | Sigler |
| 5,792,120 | A |   | 8/1998  | Menyhay |
| 5,817,344 | A |   | 10/1998 | Hoang et al. |
| 6,045,539 | A |   | 4/2000  | Menyhay |
| 6,708,363 | B2 |  | 3/2004  | Larsen |
| 6,911,025 | B2 | * | 6/2005  | Miyahara ....................... 604/415 |
| 6,994,315 | B2 | * | 2/2006  | Ryan et al. ................... 251/149.6 |

(Continued)

*Primary Examiner* — Bhisma Mehta
*Assistant Examiner* — Andrew Gilbert
(74) *Attorney, Agent, or Firm* — Jeanne Lukasavage; Craig Metcalf; Kirton McConkie (57) ABSTRACT

Cap and cleaning devices antiseptically maintain patient fluid line access valves to minimize the risk of infection via catheters. The devices have a cap that may contain a dry pad impregnated with an antimicrobial agent. The cap covers the access portion of the access valve when not in use. The devices have a hood that contains a wet pad impregnated with a cleaning solution and, optionally, an antimicrobial agent. The wet pad cleans the access portion of the access valve prior to and optionally, after the access valve is utilized to access the patient fluid line.

11 Claims, 7 Drawing Sheets

U.S. PATENT DOCUMENTS

| | | |
|---|---|---|
| 7,083,605 B2 | 8/2006 | Miyahara |
| 7,198,611 B2 | 4/2007 | Connell et al. |
| 7,282,186 B2 | 10/2007 | Lake, Jr. et al. |
| 7,452,349 B2 | 11/2008 | Miyahara |
| 7,704,935 B1 | 4/2010 | Davis et al. |
| 7,828,186 B2 | 11/2010 | Wales |
| 7,922,701 B2 | 4/2011 | Buchman |
| 8,065,773 B2 | 11/2011 | Vaillancourt et al. |
| 8,113,731 B2 | 2/2012 | Cable, Jr. et al. |
| 2004/0004019 A1* | 1/2004 | Busch ............ 206/571 |
| 2005/0124970 A1* | 6/2005 | Kunin et al. ............ 604/508 |
| 2006/0030827 A1 | 2/2006 | Raulerson et al. |
| 2007/0112333 A1 | 5/2007 | Hoang et al. |
| 2007/0202177 A1 | 8/2007 | Hoang |
| 2007/0225660 A1 | 9/2007 | Lynn |
| 2008/0027399 A1 | 1/2008 | Harding et al. |
| 2008/0147047 A1 | 6/2008 | Davis et al. |
| 2008/0177250 A1* | 7/2008 | Howlett et al. ............ 604/533 |
| 2009/0028750 A1 | 1/2009 | Ryan |
| 2009/0062766 A1* | 3/2009 | Howlett et al. ............ 604/411 |
| 2009/0149819 A1* | 6/2009 | Chelak ............ 604/246 |
| 2009/0175759 A1 | 7/2009 | Davis et al. |
| 2010/0047123 A1* | 2/2010 | Solomon et al. ............ 422/28 |
| 2010/0049170 A1* | 2/2010 | Solomon et al. ............ 604/539 |
| 2012/0039765 A1* | 2/2012 | Solomon et al. ............ 422/292 |

* cited by examiner

PATIENT FLUID LINE ACCESS VALVE ANTIMICROBIAL CAP/CLEANER

CROSS-REFERENCE TO RELATED APPLICATION(S)

This application is a divisional of application Ser. No. 11/281,711, filed Nov. 17, 2005.

BACKGROUND OF THE INVENTION

Catheter-related bloodstream infections are caused by bacteria/fungi in patients with intravascular catheters. These infections are an important cause of illness and excess medical costs, as approximately 80,000 catheter-related bloodstream infections occur in U.S. intensive care units each year. In addition to the monetary costs, these infections are associated with anywhere from 2,400 to 20,000 deaths per year.

Guidelines from the Centers for Disease Control and Prevention describe various ways to limit catheter-related bloodstream infections in hospital, outpatient and home care settings. The guidelines address issues such as hand hygiene, catheter site care and admixture preparation. Despite these guidelines, catheter-related bloodstream infections continue to plague our healthcare system.

Impregnating catheters with various antimicrobial agents is one approach that has been implemented to prevent these infections. These catheters, however, have given less than satisfactory results. In addition, some microbes have developed resistance to the various antimicrobial agents in the system.

In another system that is commercially available in Europe, a catheter hub containing an antiseptic chamber is filled with three percent iodinated alcohol. Though it has shown to be effective, the catheter hub is expensive and does not fare as well in a formal cost-benefit analysis. Therefore, there is a need for an effective and inexpensive way to reduce the number of catheter-related infections.

BRIEF SUMMARY OF THE INVENTION

The present invention is a device for antiseptically maintaining a patient fluid line access valve. The device includes a housing for covering the access portion of the access valve. A pad within the housing contacts the surface of the access portion of the access valve prior to (and optionally after) accessing the patient fluid line via the access valve to reduce the amount of microbes on the valve's access portion.

DETAILED DESCRIPTION

Figure 1:
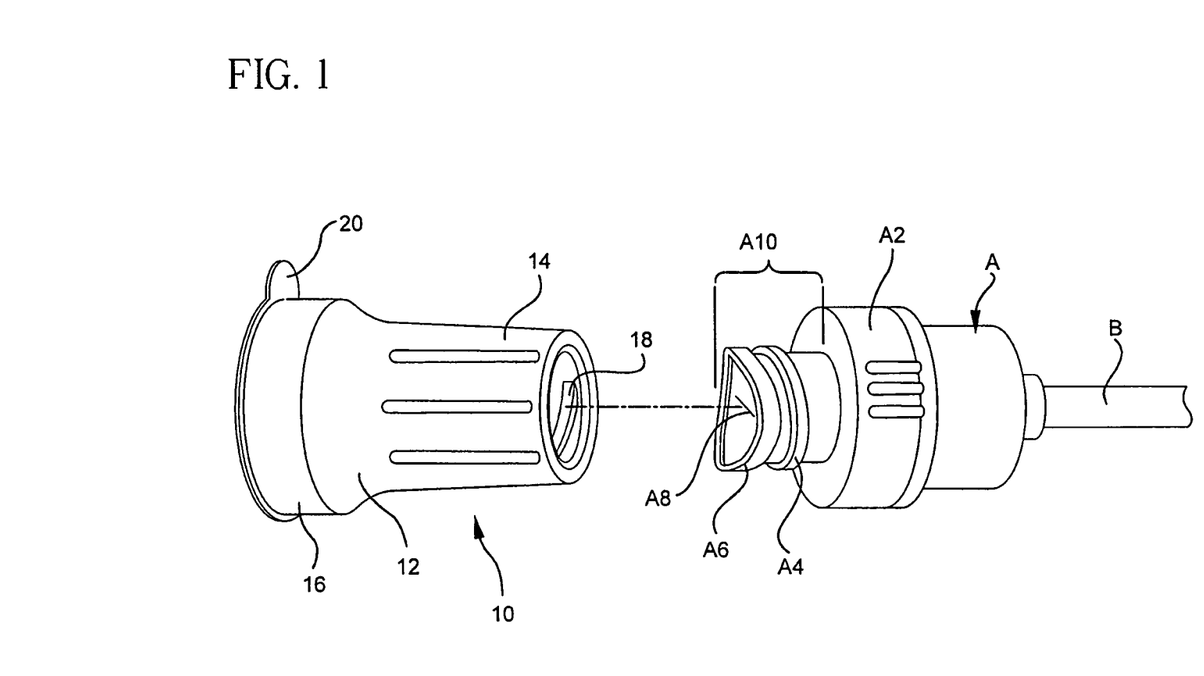
FIG. 1 is an exploded view of a first representative embodiment of a cap/cleaner device and a patient fluid line access valve.

FIG. 1 shows an exploded view of patient fluid line access valve cap/cleaner device 10 with patient fluid line access valve A and patient fluid line B. Cap/cleaner 10 includes housing 12 with cap end 14, cleaning end 16 and thread 18; and lid 20. Access valve A includes housing A2 with thread A4 and septum A6 with slit A8. The exposed surface of septum A6 along with at least a portion of the exposed surface of housing A2 that surrounds septum A6, form access portion A10 of access valve A. Line B may be any of a number of types that include, for example, intravascular (IV) lines and catheters, saline wells, arterial lines and hemodialysis lines.

As will be described in more detail below, cap end 14 of cap/cleaner 10 attaches to access portion A10 of access valve A. Housing 12 is made from any of a number of types of plastic materials such as polycarbonate, polypropylene, polyethylene, glycol-modified polyethylene terephthalate, acrylonitrile butadiene styrene or any other moldable plastic material used in medical devices.

Cap end 14 of housing 12 is open and contains thread 18 along the inside of the opening. Cleaning end 16 is covered by lid 20. Lid 20 is typically made of foil or similar type material and completely seals the opening (not shown) of cleaning end 16. Any type of material or seal may be used as long as a moisture barrier is provided.

Figure 2:
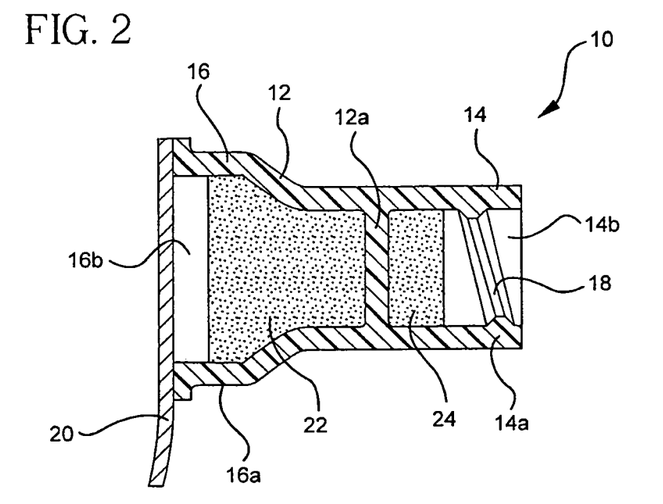
FIG. 2 is a cross-sectional side view of the first representative embodiment of the cap/cleaner device.

FIG. 2 shows cap/cleaner 10 in more detail. In addition to the structures shown in FIG. 1, cap/cleaner 10 also includes internal wall 12a, hood 16a and chamber 16b of cleaning end 16, cap 14a and cavity 14b of cap end 14, wet pad 22 within chamber 16b and dry pad 24 within cavity 14b. Internal wall 12a separates cap end 14 and cleaning end 16.

Cap/cleaner 10 is typically distributed and stored in a sterile, sealed package either alone or paired with a patient fluid line access valve. One such type of valve is the BD Q-Syte™ valve from Becton, Dickinson and Company (illustrated in FIG. 1). However, cap/cleaner 10 is useful with any type of needleless or needle-required access valve. Once removed from the package, cap/cleaner 10 is ready for use.

Figure 3:
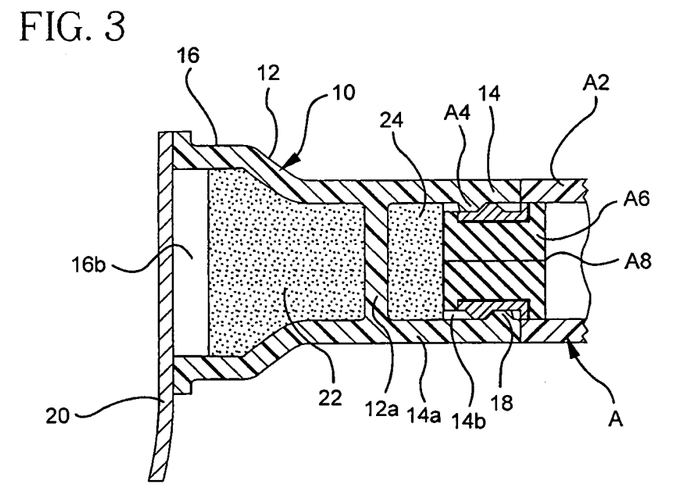
FIG. 3 is a cross-sectional side view of the first cap/cleaner device capping a patient fluid line access valve.

FIG. 3 illustrates cap/cleaner 10 covering access portion A10 of access valve A. Septum A6 provides an accessible seal for either a needle or a male luer taper. In the case of a needleless access device, such as that shown in FIG. 3, slit A8 extends through septum A6 to provide a port for insertion of the male luer taper.

As shown, cap end 14 includes cap 14a with cavity 14b, which contains dry pad 24. Dry pad 24 is impregnated with an antimicrobial agent to aid in maintaining antiseptic conditions of access portion A10 of valve A. Suitable material for dry pad 24 includes non-woven material or a foam sponge pad made of polyurethane, polyester, cotton or any bioengineered plastic material such as silicone. Any of a number of antimicrobial agents may be used to impregnate dry pad 24. Some examples include chlorhexidine gluconate, chlorhexidine diacetate, chloroxylenol, povidone iodine, Triclosan, benzethonium chloride, benzalkonium chloride, octenidine, antibiotic, etc. Alternatively, cap end 14 does not contain dry pad 24 and aids in maintaining antiseptic conditions by simply covering access portion A10.

In use, cap end 14 of cap/cleaner 10 is placed over access portion A10 such that access portion A10 is within cavity 14b of cap end 14. Cap/cleaner 10 may be attached either prior to or after placement of valve A for the patient. As shown in FIG. 3, valve A includes thread A4. By rotating cap/cleaner 10 or valve A relative to one another, threads A4 and 18 (of cap/cleaner 10) interlock to provide a secured attachment. It is not necessary, however, for valve A to include thread A4. Cap end 14 will also attach and hold a luer slip, which does not have a thread. In other embodiments, cap/cleaner 10 may be manufactured without a thread.

The amount of material used for dry pad 24 can vary. Typically, there is enough material for dry pad 24 to contact at least septum A6 of valve A. Enough space should be left in cavity 14b of cap end 14 for access portion A10 of valve A to be encompassed by cap end 14, thus, maintaining antiseptic conditions of the surface. By maintaining antiseptic conditions of the surface, the risk of microbes penetrating into valve A is minimized.

Figure 4:
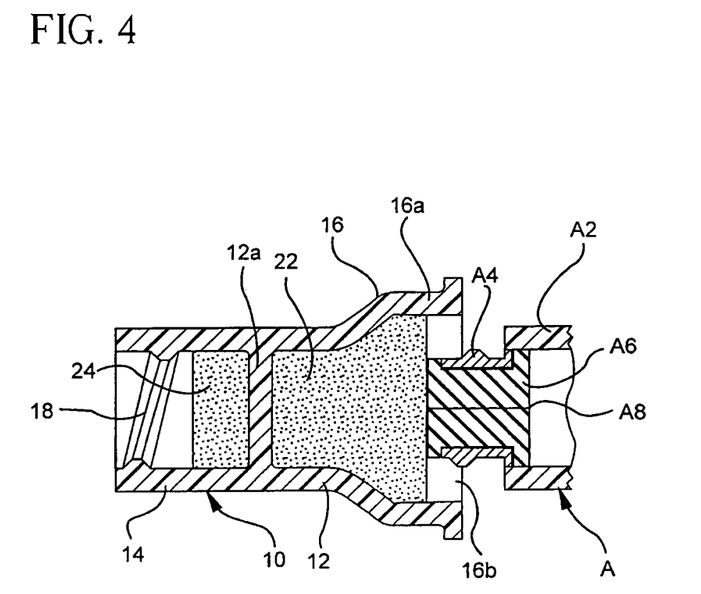
FIG. 4 is a cross-sectional side view of the first cap/cleaner device cleaning a patient fluid line access valve.

To further minimize the opportunity for penetration by microbes, access portion A10 is cleaned prior to accessing valve A with a needle or male luer taper. FIG. 4 illustrates cap/cleaner 10 cleaning access portion A10 of valve A.

As shown in FIG. 4, cleaning end 16 includes hood 16a and chamber 16b, which contains wet pad 22. Wet pad 22 is impregnated with a cleaning agent and optionally, an antimicrobial agent. Wet pad 22 may be made from materials similar to those described for dry pad 24.

The cleaning solution is typically an alcohol- or water-based solution. A suitable alcohol-based solution contains about 50% to about 100% (no additional water) of an alcohol solution. The balance of solutions that are less than 100% alcohol contain water and other optional materials such as fragrance, dye, surfactant, emollient, etc.

Suitable water-based solutions contain about 1% to about 10% alcohol solvent as a wetting agent and about 90% to about 99% water. Again, optional materials may also be added such fragrance, dye, surfactant, emollient, etc.

In an alternative embodiment, the cleaning solution also includes an antimicrobial agent. Any of a number of antimicrobial agents may be used in wet pad 22. Some examples include chlorhexidine gluconate, chlorhexidine diacetate, chloroxylenol, povidone iodine, Triclosan, benzethonium chloride, benzalkonium chloride, octenidine, antibiotic, etc. Wet pad 22 and dry pad 24 may be impregnated with the same or different antimicrobial agents.

As shown in the Figures, cleaning end 16 is larger than cap end 14. The hood of cleaning end 16 loosely encompasses at least access portion A10 of valve A, and chamber 16b is sized to allow some movement when access portion A10 is inserted. The amount of material used for wet pad 22 will vary, but the amount should hold enough cleaning solution and allow enough movement for thorough cleaning. Wet pad 22 should be contained entirely within hood 16a such that it is recessed inside chamber 16b of cleaning end 16.

In preparation for accessing valve A, cap end 14 is removed from valve A either by rotating cap/cleaner 10 to release threads 18 and A4 or by simply pulling if valve A does not have a thread. Lid 20 is removed from cleaning end 16. Cleaning end 16 is then placed over at least access portion A10, such that wet pad 22 contacts septum A6. Though FIG. 4 only shows contact with septum A6, additional pressure may be applied such that wet pad 22 extends beyond the edges of septum A6 to contact portions of the exposed surface of housing A2.

Next, for thorough cleaning, wet pad 22 should scrub access portion A10 of valve A. Scrubbing may be accomplished by, for example, rotational movement or back and forth movement. Scrubbing should be carried out for a time long enough to allow the cleaning solution to at least disinfect access portion A10 of valve A.

Once cleaned, valve A is ready to use. A needle or male luer taper is inserted to either infuse or withdraw fluid from the patient fluid line.

Figure 5:
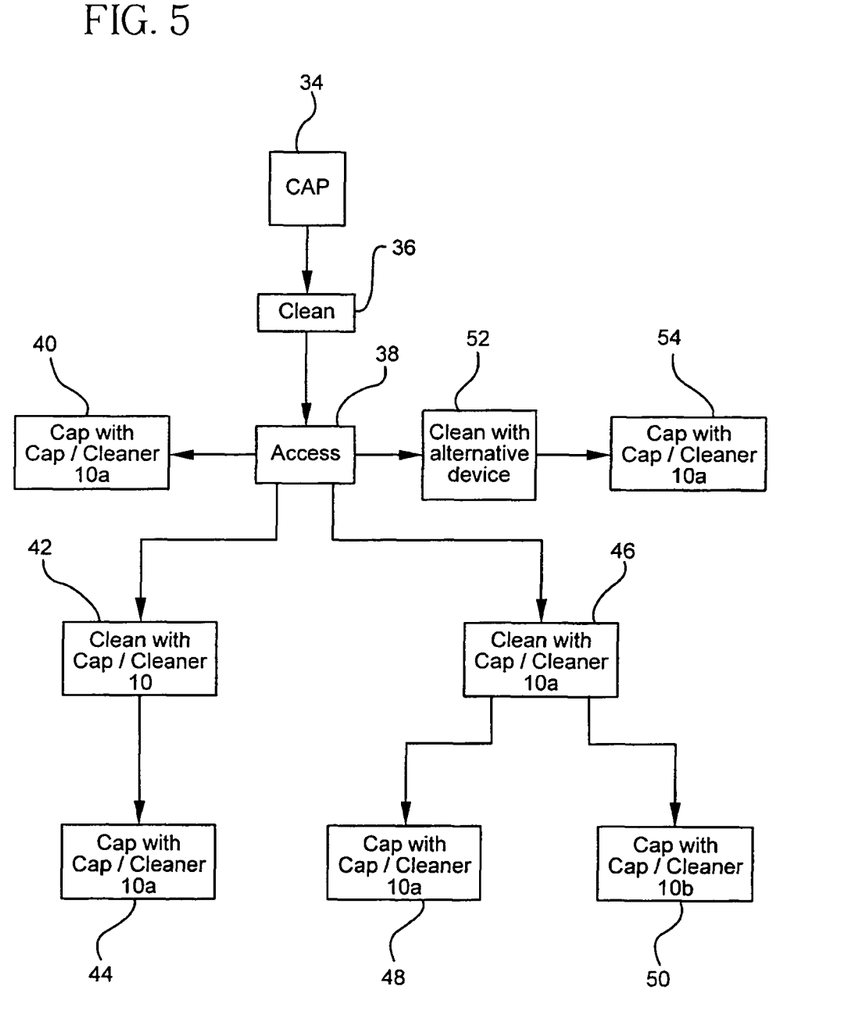
FIG. 5 is a flow chart illustrating representative embodiments of methods of using the cap/cleaner device.

FIG. 5 is a flowchart illustrating representative embodiments of methods for using cap/cleaner 10. Capping step 34, cleaning step 36 and accessing step 38 were described above and are the same in each embodiment. However, upon withdrawal after accessing the patient fluid line, access portion A10 of valve A may either be immediately capped or cleaned again prior to capping. If immediately capped, a new, second cap/cleaner 10a is obtained and removed from its package. This is represented by step 40. Cap end 14 of cap/cleaner 10a is placed over access portion A10 as described above. Cleaning end 16 of cap/cleaner 10a is sealed and ready for the next time valve A is utilized.

Alternatively, access portion A10 may be cleaned again prior to capping. This can be performed in one of the following ways. First, in step 42, cleaning end 16 of cap/cleaner 10 is reused to clean access portion A10, which is then capped, at step 44, with cap end 14 of a new, second cap/cleaner 10a. Second, in step 46, cleaning end 16 of a new, second cap/cleaner 10a is used to clean access portion A10. Then, valve A may be capped either with cap end 14 of cap/cleaner 10a (step 48) or of a new, third cap/cleaner 10b (step 50). Third, in step 52, access portion A10 may be cleaned with an alternative disposable cleaning device that is well known in the art. Examples of such cleaning devices include alcohol wipes, iodine swabs, etc. Once cleaned, cap end 14 of a new, second cap/cleaner 10a may be attached to valve 26 (step 50).

Figure 6:
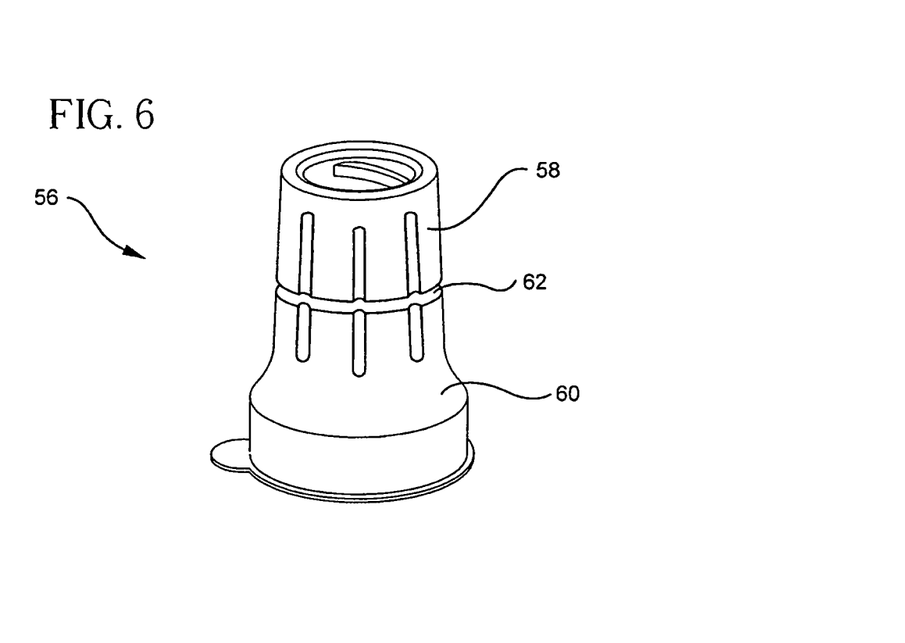
FIG. 6 is a perspective view of a second representative embodiment of a cap/cleaner device.

Additional embodiments of the present invention include separable and individual, uncoupled devices. FIG. 6 shows separable cap/cleaner 56. Separable cap/cleaner 56 includes cap end 58, cleaning end 60 and gap 62. Gap 62 is the separation between cap end 58 and cleaning end 60.

Figure 7:
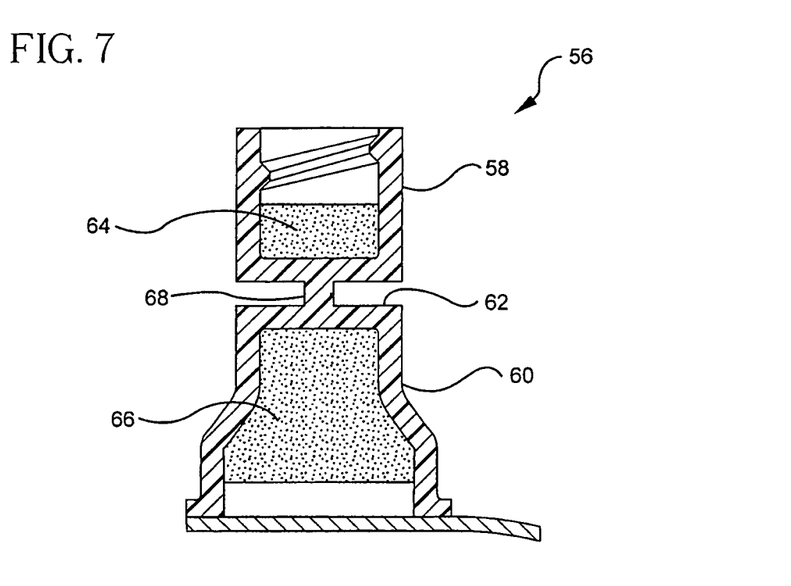
FIG. 7 is a cross-sectional side view of the second cap/cleaner device.

FIG. 7 shows separable cap/cleaner 56 in more detail and further includes dry pad 64 within cap end 58, wet pad 66 within cleaning end 60 and breakable connector 68. In use, separable cap/cleaner 56 operates as described above for cap/cleaner 10 except that cleaning end 60 may be removed after cleaning access portion A10 of valve A. Detaching cleaning end 60 reduces bulkiness from separable cap/cleaner 56 by only maintaining cap end 58 over access portion A10.

Figure 8:
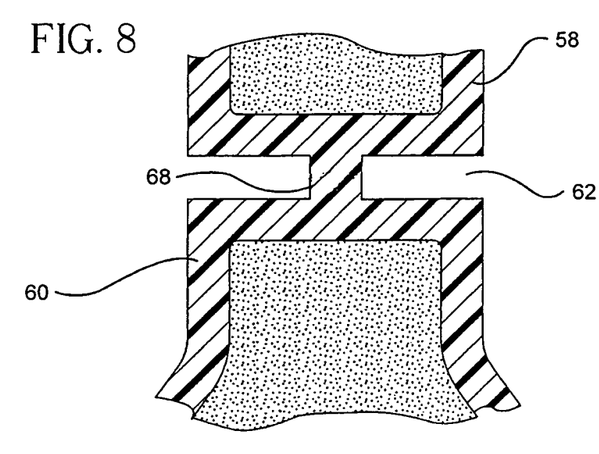
FIG. 8 is a cross-sectional view of a first separable connector.

FIG. 8 shows a representative embodiment of breakable connector 68. Connector 68 is typically made of the same material from which housing 12 is fabricated. Torsional shearing caused by twisting cap end 58 and/or cleaning end 60 relative to each other may be used to break connector. Alternatively, a three-point bending force, which consists of a fulcrum (connector 68) that directs a force vector contralateral to the direction of the terminal (cap end 58 and cleaning end 60) force vectors, may be applied for breaking connector 68. Once removed, cleaning end 60 may be discarded.

Figure 9:
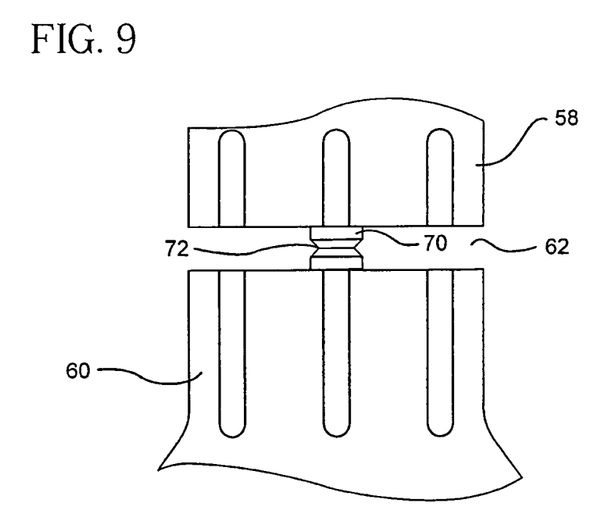
FIG. 9 is a side view of a second separable connector.

FIG. 9 is an alternate embodiment showing notched breakable connector 70. Notch 72 within connector 70 is an area of reduced cross-sectional area, which acts as a score to facilitate breaking of connector 70.

Other separation mechanisms may also be used to remove cleaning end 60 from cap end 58. For instance, a luer lock type mechanism can be utilized to separate ends 58 and 60 from each other.

Figure 10A:
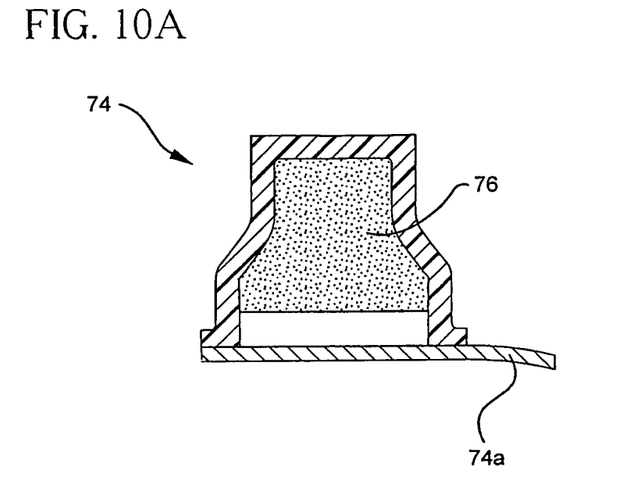
FIG. 10A is a cross-sectional view of cleaning device.

FIG. 10A shows a representative embodiment of cleaning device 74 with lid 74a and wet pad 76. Here, cleaning device 74 is a stand-alone device that is used as described above for cleaning end 16.

Figure 10B:
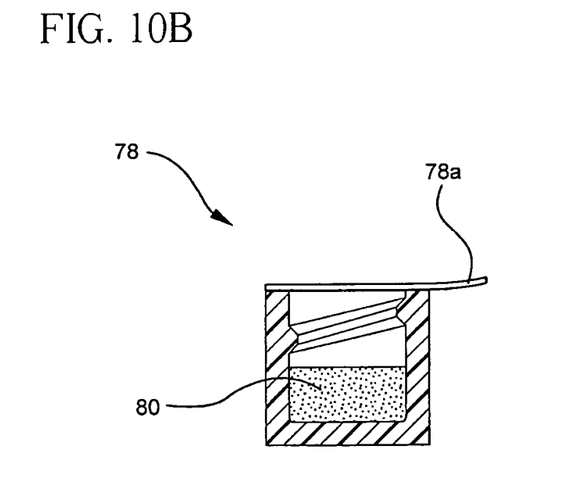
FIG. 10B is a cross-sectional view of a capping device.

FIG. 10B shows a representative embodiment of cap device 78 with lid 78a and pad 80. Cap device 78 is a standalone device where pad 80 may either be a wet pad or a dry pad. Where pad 80 is a dry pad, cap device 78 is used as described above for cap end 14.

Where pad 80 is a wet pad, cap device 78 may be used to clean access portion A10 of valve A in addition to its capping function. The twisting motion involved in removing and placing cap device 78 with respect to access potion A10 provides friction for cleaning. Additional cleaning can be accomplished by twisting cap device 78 in one direction and then in the reverse direction for a desired amount of time.

With either cleaning device 74 or cap device 78, additional gripping surface may be added by extending the length of the housing. The increased gripping surface would provide easier handling of devices 74 and 78.

Cap/cleaner 10 cleans and maintains access valves in antiseptic or aseptic condition. This substantially decreases the risk of patient infections caused by the ingress of microbes into the access valves, particularly for needleless access valves.

Although the present invention has been described with reference to preferred embodiments, workers skilled in the art will recognize that changes may be made in form and detail without departing from the spirit and scope of the invention.

What is claimed is:

1. A cap device for reducing risk of contamination of a patient fluid line access valve, the cap device comprising:
   a first cavity for retaining a first pad, the first pad comprising a first cleaning solution, the first cavity further comprising a set of threads for threadedly receiving a set of threads of the patient fluid line access valve such that an access portion of the patient fluid access valve contacts the first pad;
   a second cavity for retaining a second pad comprising a second cleaning solution, the second cavity having an opening through which the access portion of the patient fluid access valve may be inserted to temporarily contact the second pad; and
   an internal wall interposed between the first and second cavities.

2. The cap device of claim 1 wherein the first and second cleaning solutions comprise an antimicrobial agent.

3. The cap device of claim 2 wherein the first cleaning solution is different than the second cleaning solution.

4. The cap device of claim 1 wherein the internal wall comprises a breakable connector.

5. The cap device of claim 1 and further comprising:
   a lid sealing the second pad within the second cavity.

6. The cap device of claim 1 further comprising a housing in which the first and second cavities are provided.

7. A method of reducing risk of contamination of a patient fluid line access valve, the method comprising:
   inserting an access portion of the patient fluid line access valve into a first cavity of a cap device, the first cavity having a first pad comprising a first cleaning solution, the first cavity having an opening through which an access portion of the patient fluid access valve may be inserted to temporarily contact the first pad; and
   attaching a second cavity of the cap device to the access portion of the patient fluid line access valve, the second cavity having a second pad comprising a second cleaning solution, the second cavity further comprising a set of threads for threadedly receiving a set of threads of the patient fluid line access valve such that the access portion of the patient fluid access valve contacts the second pad, the cap device further comprising an internal wall separating the first and second cavities.

8. The method of claim 7 and further comprising:
   removing the access portion of the patient fluid access valve from the first cavity prior to attaching the second cavity of the cap device to the access portion of the patient fluid line access valve.

9. The method of claim 7, wherein the first cleaning solution is different than the second cleaning solution.

10. The method of claim 7 and further comprising:
    removing a lid from at least one of the first and second cavities prior to inserting or attaching the access portion of the patient fluid line access valve to the respective cavity.

11. The method of claim 7, wherein the cleaning solutions of the first and second pads comprise an antimicrobial agent.

\* \* \* \* \*